United States Patent [19]

Watanabe et al.

[11] 4,240,890
[45] Dec. 23, 1980

[54] OXYGEN PARTIAL PRESSURE MEASURING DEVICE SUITABLY ADAPTED FOR INTERNAL COMBUSTION ENGINE EXHAUST GASES

[75] Inventors: Tetsuo Watanabe, Nagoya; Shigetaka Wada, Kuwana; Shigeo Soejima, Nagoya, all of Japan

[73] Assignee: NGK Insulators, Ltd., Nagoya, Japan

[21] Appl. No.: 11,765

[22] Filed: Feb. 12, 1979

Related U.S. Application Data

[63] Continuation of Ser. No. 846,185, Oct. 26, 1977, abandoned.

[30] Foreign Application Priority Data

Oct. 29, 1976 [JP] Japan .................................. 51/129335

[51] Int. Cl.³ ............................................ G01N 27/58
[52] U.S. Cl. ................................................. 204/195 S
[58] Field of Search .............. 204/195 S, 1S; 60/276; 123/119 E; 324/71 R, 29; 422/98

[56] References Cited

U.S. PATENT DOCUMENTS

| | | | |
|---|---|---|---|
| 3,926,851 | 12/1975 | Sergeys | 252/477 R X |
| 3,935,089 | 1/1976 | Togawa et al. | 204/195 S |
| 3,981,785 | 9/1976 | Sandler | 204/195 S |
| 4,007,589 | 2/1977 | Neidhard et al. | 60/276 |
| 4,042,738 | 8/1977 | Gulati | 252/477 R X |
| 4,061,713 | 12/1977 | Weidenbach et al. | 252/466 PT X |
| 4,132,615 | 1/1979 | Linder et al. | 204/195 S |

FOREIGN PATENT DOCUMENTS 2416629  10/1975  Fed. Rep. of Germany ....... 204/195 S

*Primary Examiner*—G. L. Kaplan
*Attorney, Agent, or Firm*—Stevens, Davis, Miller & Mosher

[57] ABSTRACT

An oxygen partial pressure measuring device for determining oxygen partial pressures in exhaust gases emitted from internal combustion engines comprises a metallic vessel mounted within an exhaust pipe of the engine and having an exhaust gas inlet facing to the exhaust gas flow and an exhaust gas outlet formed in a side surface of the vessel, an oxygen concentration cell shutting the exhaust gas out of the air in an air-tight manner, and a monolithic structure, what is called a honeycomb structure, located between the exhaust gas inlet and the oxygen concentration cell within the vessel for burning the exhaust gas.

7 Claims, 9 Drawing Figures

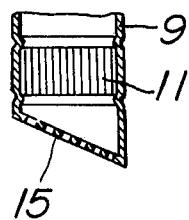
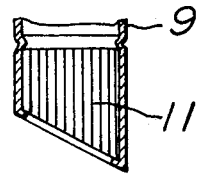
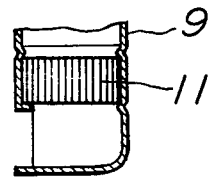
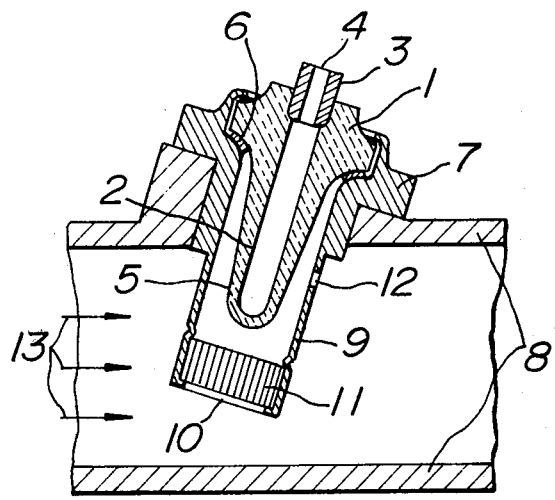

OXYGEN PARTIAL PRESSURE MEASURING DEVICE SUITABLY ADAPTED FOR INTERNAL COMBUSTION ENGINE EXHAUST GASES

This is a continuation of application Ser. No. 846,185 filed Oct. 26, 1977 and now abandoned.

BACKGROUND OF THE INVENTION (1) Field of the Invention

The present invention relates to an oxygen partial pressure measuring device for determining oxygen partial pressure in exhaust gases, especially gases discharged from internal combustion engines.

(2) Description of the Prior Art

It has been known to provide conductive electrodes, such as platinum, on opposite faces of an oxygen ion conductive solid electrolytic partition made of, for example, stabilized zirconia, one electrode having a surface (first surface) adapted to be in contact with a reference atmosphere having a known oxygen partial pressure such, for example, as the air and the other electrode having a surface (second surface) adapted to be in contact with gas to be measured, for example, exhaust gas of an internal combustion engine, to provide an oxygen concentration cell at high temperatures the electromotive force of which is indicated by the Nernst equation, $E = RT/nF \ln P_1/P_2$ under ideal conditions, where E is electromotive force; T is absolute temperature; $P_1$ and $P_2$ are oxygen partial pressures in atmospheres contacting the first and second surfaces of the partition; R is gas constant; F is Faraday's constant; and n is charge of cation of the solid electrolyte. Such a cell could be used as an oxygen partial pressure measuring device for determining oxygen partial pressures in gases to be measured.

With exhaust gases of internal combustion engines, the oxygen partial pressure therein in a state of equilibrium is relatively high, if the excess air ratio in the exhaust gas components is more than one. However, in the event that the excess air ratio is less than one, the oxygen partial pressure is considerably low. The electromotive force of the oxygen concentration cell rapidly changes across the line of the excess air ratio one. Such a great change in electromotive force is very advantageous for controlling or maintaining the excess air ratio of the exhaust gas at one for the purpose of using the electromotive force as signals.

With the usual exhaust gases of internal combustion engines, however, they are not necessarily in the state of equilibrium because unburnt fuel gases and unreacted oxygen co-exist. In order to cause the electromotive force of the oxygen concentration cell to vary rapidly across the line of the excess air ratio one, it is required to bring the exhaust gas contacting the second surface of the cell into an equilibrium condition. Electrodes made of platinum could achieve this purpose to some extent owing to the catalytic action of platinum. However, the thickness of the platinum layer as the electrode is generally so thin that the time for the passage of the exhaust gas through the electrode layer is very short. Accordingly, catalytic action of the platinum electrode is, by itself, insufficient to bring the exhaust gas into the equilibrium condition, when the exhaust gas includes large amounts of unburnt fuel gas and oxygen. In particular, with an exhaust gas cleaning system wherein an internal combustion engine is operated at an excess air ratio less than one and secondary air is introduced into the exhaust gas to increase the excess air ratio to one, the electromotive force of the oxygen concentration cell does not change rapidly at the excess air ratio one because of the large amounts of the unburnt fuel gas and oxygen in the exhaust gas.

In order to solve this problem, it has been suggested that a porous film having a catalytic action be applied onto the second surface of the electrode to supplement the catalytic action. In this method, however, the thickness of the catalytic porous film is at the most 1 mm, so that the catalytic action is quite insufficient to bring the exhaust gas into the equilibrium condition in the event of great amounts of unburnt components in the exhaust gas, although it is effective to some extent for the exhaust gas near the equilibrium. When the thickness of the porous film having the catalytic action is made thicker in order to avoid this disadvantage, the response time will in turn become lower to an extent such that it cannot be used for practical purposes.

It has also been suggested that a catalyst carried on a granular carrier or mineral wool be arranged against the exhaust gas flow in front of the detecting end of a device so that the oxygen partial pressure is determined after the exhaust gas has passed through the catalyst to bring it into an equilibrium condition. This method complicates mounting and replacing the catalyst bed onto and from the exhaust pipe and requires a great amount of the catalyst bed which makes the head of the exhaust pipe larger and causes loss in weight of the catalyst bed due to vibrations. Moreover, the flow passages of the exhaust gases in the catalyst bed are not fixed, so that the times required for the exhaust gases to pass through the catalyst bed vary within a wide range, with the result that the composition of the exhaust gas varies for a short period of time and the output of the oxygen concentration cell does not respond sufficiently to the variation in the composition of the exhaust gas for the short period of time.

SUMMARY OF THE INVENTION

A primary object of the invention is, therefore, to provide an oxygen partial pressure measuring device for determining partial pressures in exhaust gases, which eliminates the disadvantages of the hitherto used oxygen partial pressure measuring devices.

A further object of the invention is to provide an improved oxygen partial pressure measuring device, which is small in size, easy to install and replace, and highly responsive to variations in compositions of exhaust gases and which can determine the oxygen partial pressure by bringing nonequilibrium exhaust gases into equilibrium using a small amount of catalyst layer.

The oxygen partial pressure measuring device according to the present invention comprises a monolithic structure and a cylindrical body accommodating therein and fixing thereto an oxygen concentration cell and the monolithic structure such that exhaust gas to be measured reaches said oxygen concentration cell after it has passed through the monolithic structure.

It will be understood that the expression "monolithic structure" used herein means what is called the honeycomb structure formed with a multiplicity of substantially parallel channels therethrough and these channels are separated from each other by partitions. The channels may have a circular, triangular, rectangular, or hexagonal or other crosssection and may be free in size or any combination of these shapes or sizes and may be curved.

The device comprising the monolithic structure according to the invention can determine the equilibrium partial pressures of nonequilibrium exhaust gases according to the following reason. The unburnt gases such as lower hydrocarbon, carbon monoxide and the like included in exhaust gases discharged from internal combustion engines can be inherently burnt with oxygen at temperatures above approximately 400° C. at which the oxygen concentration cell with the oxygen ion conductive solid electrolyte operates. With a system introducing secondary air into exhaust gases, however, the unburnt gases and air are not sufficiently mixed, so that the exhaust gases could not be in the equilibrium condition. The nonequilibrium exhaust gases are burnt and come under the equilibrium condition while they are passing through the monolithic structure. The exhaust gases pass smoothly through the monolithic structure without staying so that the equilibrium oxygen partial pressure can be rapidly determined no matter how the compositions of exhaust gases vary. The monolithic structure eliminates the abrasion due to vibration which would occur in granular carriers for catalyst. The monolithic structure may easily be united with a metallic vessel and has less pressure loss in the vessel.

The material of the monolithic structure is preferably, for example, cordierite which is a ceramic having high thermal shock resistance. The monolithic structure may be made of other materials having the required heat resistance and thermal shock resistance.

The configuration of the monolithic structure may be selected in consideration of the gas mixing effect and pressure losses. In the case of the ceramic monolithic structure, it may be made of only a refractory such as cordierite, mullite, alumina and the like. It is preferable for the monolithic structure of these refractories to carry catalysts such as platinum, palladium, platinum alloy or composites of cooper oxide and chromic oxide including nickel oxide which are more effective to bring the nonequilibrium exhaust gases into equilibrium condition.

The monolithic structure itself may of course be made of a material having oxidizing catalytic action such as a composite of copper oxide and chromic oxide including nickel oxide or a composite of lanthanum oxide and cobalt oxide including strontium oxide or made of a ceramic including a material having oxidizing catalytic action distributed in the ceramic.

Moreover, a plurality of monolithic structures may be arranged in rows or spaced apart to provide spaces therebetween if desired. The channels of the monolithic structure are arranged staggered to increase the gas mixing effect at the jointed surfaces.

BRIEF DESCRIPTION OF THE DRAWING

These and other objects and advantages of the invention may be readily ascertained by referring to the following description and appended drawings in which:

FIGS. 3-5 are sectional views showing embodiments of the exhaust gas inlet at the end of the device according to the invention;

FIG. 6 is a sectional view of the other embodiment of the device according to the invention;

DETAILED DESCRIPTION OF THE PREFERRED EMBODIMENT

Figure 1:
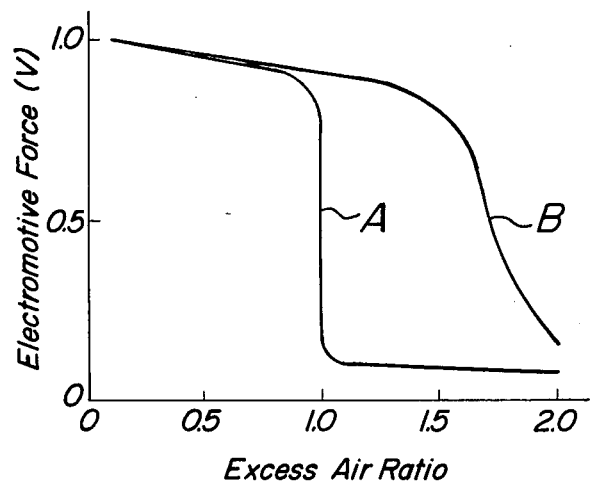
FIG. 1 is an explanatory representation showing the relation between the excess air ratio of exhaust gases and the electromotive force of the oxygen concentration cell with solid catalyst.

Referring to FIG. 1 illustrating the relation between the electromotive force of an oxygen concentration cell and the excess air ratio of exhaust gases, the electromotive force rapidly changes across the line where the excess air ratio is one as shown in the curve A in FIG. 1. Such a great change in electromotive force is very advantageous for maintaining the excess air ratio of the exhaust gas at one. However, when a large amount of the unburnt fuel gas and oxygen co-exist in the exhaust gas, the electromotive force of the oxygen concentration cell does not change rapidly at the excess air ratio one as shown in the curve B of FIG. 1.

Figure 2:
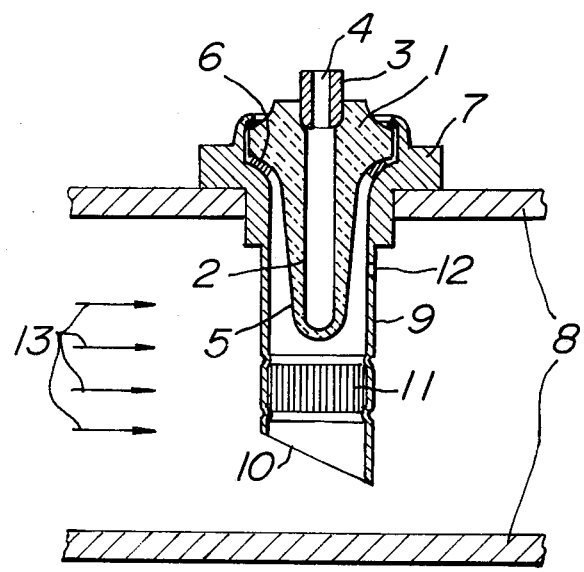
FIG. 2 is a sectional view of one embodiment of the oxygen partial pressure measuring device according to the invention.

The present invention will be explained hereinafter referring to the FIGS. 2-8, wherein the monolithic structure is ceramic. FIG. 2 illustrates one embodiment of the present invention. The apparatus shown in FIG. 2 comprises a cylindrical solid electrolyte partition 1 having one end closed, which may be of a sintered substance such as $ZrO_2$ stabilized with CaO or $Y_2O_3$, or $CeO_2$ added with $La_2O_3$. Inside the partition is an electrode 2 adapted to be in contact with the air as a reference atmosphere through a bore 4 formed in a terminal 3. Outside of the partition is an electrode 5 adapted to be in contact with the exhaust gas and electrically connected through a conductive sealing material 6 to a metallic vessel 7, which vessel 7 also serves as a terminal. The electrodes 2 and 5 are preferably made of porous platinum. The surfaces of the electrode 5 may be coated with porous protective films for protecting the electrode 5, which are ceramic less than $100\mu$ in thickness and do not substantially affect the response time. Furthermore, a catalyst such as platinum or palladium may be carried on the porous protective films. The metallic vessel 7 is secured to a wall 8 of an exhasut pipe of an internal combustion engine by means of securing means as screw threads or welding. The metallic vessel 7 includes a cylindrical portion 9 extending into the exhaust pipe and having at the end an exhaust gas inlet 10 which is oblique facing against the exhaust gas flow 13 as shown in FIG. 2. A ceramic monolithic structure 11 is fixed within the cylindrical portion 9 by caulking, adherent and the like. An exhaust gas outlet 12 is provided in the cylindrical portion 9 of the vessel 7 opening at the right angle to or opposite to the direction of the exhaust gas flow 13.

The oxygen partial pressure measuring device according to the invention is so constructed as above described that the exhaust gas at the exhaust gas inlet 10 tends to be pressurized by the exhaust gas flow 13 and at the outlet 12 to be reduced, with the result that the exhaust gas is forced to flow from the exhaust gas inlet 10 through the monolithic structure 11 where the unburnt gas is burnt and via the electrode 5 arranged on the second surface of the solid electrolyte partition 1 and through the outlet 12 out of the device.

FIGS. 3-5 illustrate other embodiments of the proximity of the exhaust gas inlet of the device according to the present invention. Referring to FIG. 3, an exhaust gas inlet comprises a disc 15 formed with a number of small holes to control the amount of the exhaust gas passing through the inlet. In the embodiment shown in FIG. 4, a monolithic structure itself has at its end an oblique surface which is substantially flush with the oblique section of the exhaust gas inlet 10. Referring to FIG. 5, a cylindrical portion 9 of a vessel 7 is provided at the lower side surface with an exhaust gas inlet directly facing to the exhaust gas flow. In the embodiment shown in FIG. 6, an entire device is arranged at an angle relative to the exhaust gas flow 13 in the exhaust pipe, so that the exhaust gas inlet 10 is tilted relative to the gas flow, although the inlet is opening in the axial direction of the cylindrical portion 9. In brief, all that is required is to provide the exhasut gas inlet so as to be subjected to a positive pressure by the exhaust gas flow.

Figure 7:
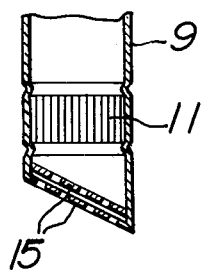
FIG. 7 is a sectional view illustrating other embodiment of the exhaust gas inlet at the end of the device according to the invention.

Moreover, as above described, the nonequilibrium exhaust gas is mixed and burned during passing through the monolithic structure and further burnt with the aid of a catalytic reaction and becomes under an equilibrium condition. In this case the mixture is important as much as the catalytic reaction. With the exhaust gas including relatively much amount of unburnt gas, therefore, it is effective to disturb the exhaust gas flow by the use of the gas inlet 10 which has a disc 15 formed with a number of small holes as shown in FIG. 3 or two discs 15, 15 each having a number of holes of which positions are shifted to each other as shown in FIG. 7 and it is also preferable to provide appropriate gas homogenizing spaces between the exhaust gas inlet and monolithic structure and between the monolithic structure and oxygen concentration cell for homogenizing the disturbed exhaust gas flow.

The amount of the exhaust gas flowing through the device according to the invention is depending mainly upon the positive pressure acting upon the exhaust gas inlet, the negative pressure at the exhaust gas outlet, and the pressure losses at the exhaust gas inlet, monolithic structure and exhaust gas outlet. As described above, since there is no tendency for the exhaust gas to stay in the device, it is not required to cause an excess exhaust gas to flow through the device according to the invention but it is only required to limit the necessary and sufficient amount of exhaust gas passing through the device to improve the durabilities of the catalyst carried on the monolithic structure, external electrodes of the oxygen concentration cell and protective layers on the external electrodes. For this purpose it is preferable to limit the exhaust gas passing through the device to an extent such that the total of the pressure losses at the exhaust gas inlet and outlet is more than the pressure loss at the monolithic structure, because it is absolutely necessary for the monolithic structure to have determined surface areas and opening area ratio in order to exhibit the exhaust gas mixing and burning effects. A high pressure loss at the monolithic structure would adversely affect the effect of the present invention.

Figure 8A:
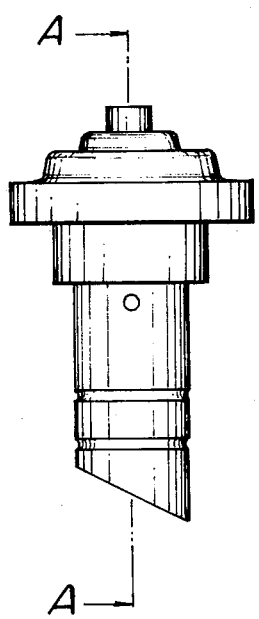
FIGS. 8a and 8b are front and sectional views of the other embodiment of the device according to the invention.
Figure 8B:
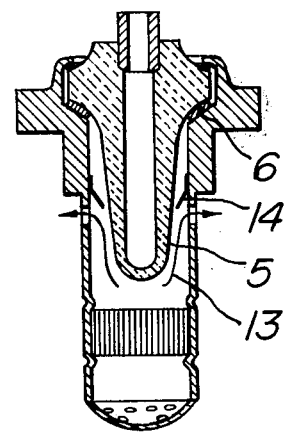

As shown in FIGS. 8a and 8b, a baffle board 14 may be provided for the purpose of causing the high temperature exhaust gas 13, which has passed through the monolithic structure and passed by the electrode 5 of the oxygen concentration cell adapted to be in contact with the exhaust gas, to flow smoothly towards the exhaust gas outlet without flowing toward the conductive sealing material 6. If the high temperature exhaust gas contacted the sealing material 6 sealing the electrode 5 from the air in an air-tight manner, the tight sealing of the material 6 would be affected.

The solid electrolyte partition may be in the form of a disc or cylindrical body, though it has been described as a cylinder having one closed end as shown in FIGS. 2, 6 and 8b.

The oxygen partial pressure measuring device according to the invention is so constructed as above described that the exhaust gas including much amount of unburnt gas is burnt when it passes through the monolithic structure and the burnt exhaust gas is adapted to be in contact with the solid electrolyte partition. The device itself may be detachably secured to an exhaust pipe, so that with exhaust gases under nonequilibrium condition, the equilibrium oxygen partial pressure can very easily be measured, while with equilibrium or nonequilibrium exhaust gases, accurate and rapid response of the electromotive force of the oxygen concentration cell can be obtained and the life of the cell can be elongated, which characteristics are preferable for determining the oxygen partial pressure in exhaust gases of internal combustion engines. Accordingly, the device according to the invention is very advantageous for industrial purposes because it can be utilized to obtain the complete combustion of fuels for internal combustion engines or boilers which serves to provide an effective use of the fuels and reduce the pollution resulting from the exhaust gases.

While preferred embodiments have been described, variations thereto will occur to those skilled in the art within the scope of the present inventive concepts which are delineated by the following claims.

What is claimed is:

1. In an oxygen partial pressure measuring device for determining oxygen partial pressure in exhaust gases, the device comprising a cylindrical body and an oxygen concentration cell of oxygen ion conductive solid electrolyte therein, said device to be inserted into the exhaust gas stream, the improvement comprising a monolithic structure, which is formed with a multiplicity of substantially parallel channels through which said exhaust gases are burnt and become under the equilibrium condition, accommodated within said cylindrical body and so located therein that exhaust gas to be measured reaches said oxygen concentration cell after it has passed through said monolithic structure.

2. A device as set forth in claim 1, wherein said monolithic structure has a catalytic action which oxidizes unburnt components in the exhaust gas to be measured contacting said monolithic structure.

3. A device as set forth in claim 2, wherein said catalyst consists of a ceramic catalyst carrier and a catalytic material carried thereby.

4. A device as set forth in claim 2, wherein said catalyst is of ceramics having a catalytic action.

5. A device as set forth in claim 2, wherein said catalyst is of ceramics having a catalytic material uniformly distributed therein.

6. A device as set forth in claim 1, wherein a space is provided between said oxygen concentration cell and said monolithic structure.

7. A device as set forth in claim 6, wherein a further space is provided between said one end of said cylindrical body and said monolithic structure.

* * * * *